(12) United States Patent
Moran (10) Patent No.: US 10,392,651 B2
(45) Date of Patent: Aug. 27, 2019

(54) PROCESSED BIOLOGICAL SAMPLE STORAGE

(71) Applicant: GE Healthcare UK Limited, Buckinghamshire (GB)

(72) Inventor: Nina Moran, Portishead (GB)

(73) Assignee: GE Healthcare UK Limited, Little Chalfont (GB)

( * ) Notice: Subject to any disclaimer, the term of this patent is extended or adjusted under 35 U.S.C. 154(b) by 243 days.

(21) Appl. No.: 15/119,065

(22) PCT Filed: Feb. 20, 2015

(86) PCT No.: PCT/EP2015/053620
§ 371 (c)(1),
(2) Date: Aug. 15, 2016

(87) PCT Pub. No.: WO2015/128259
PCT Pub. Date: Sep. 3, 2015

(65) Prior Publication Data
US 2017/0051334 A1    Feb. 23, 2017

(30) Foreign Application Priority Data
Feb. 28, 2014  (GB) .................................. 1403522.4

(51) Int. Cl.
| | | |
|---|---|---|
| *C12Q 1/68* | (2018.01) | |
| *B01L 3/00* | (2006.01) | |
| *C12N 15/10* | (2006.01) | |
| *C12Q 1/6806* | (2018.01) | |
| *B01L 9/00* | (2006.01) | |

(52) U.S. Cl.
CPC .......... *C12Q 1/6806* (2013.01); *B01L 3/5023* (2013.01); *B01L 3/502738* (2013.01); *B01L 9/527* (2013.01); *C12N 15/1003* (2013.01); *B01L 2200/04* (2013.01); *B01L 2200/0689* (2013.01); *B01L 2300/021* (2013.01); *B01L 2300/041* (2013.01); *B01L 2300/043* (2013.01); *B01L 2300/069* (2013.01); *B01L 2300/0816* (2013.01); *B01L 2300/123* (2013.01); *B01L 2300/126* (2013.01); *B01L 2400/0406* (2013.01); *B01L 2400/0688* (2013.01)

(58) Field of Classification Search
CPC ..... C12Q 1/6806; B01L 3/5023; B01L 9/527; C12N 15/1003
See application file for complete search history.

(56) References Cited

U.S. PATENT DOCUMENTS

| | | | |
|---|---|---|---|
| 5,496,562 A | 3/1996 | Burgoyne | |
| 7,748,283 B2 | 7/2010 | Harvey et al. | |
| 8,283,165 B2 | 10/2012 | Hogan et al. | |
| 2012/0088249 A1* | 4/2012 | Jovanovich | B01F 11/0071 435/6.12 |
| 2013/0280725 A1* | 10/2013 | Ismagilov | B01L 3/5027 435/6.12 |
| 2013/0338351 A1 | 12/2013 | Kvam et al. | |

FOREIGN PATENT DOCUMENTS

| | | |
|---|---|---|
| WO | 96/39813 A1 | 12/1996 |
| WO | 01/09389 A2 | 2/2001 |
| WO | 2004/033470 A2 | 4/2004 |
| WO | 2006/032044 A2 | 3/2006 |
| WO | 2010/091414 A2 | 8/2010 |
| WO | 2013/024072 A1 | 2/2013 |
| WO | 2013/159117 A1 | 10/2013 |

OTHER PUBLICATIONS

European Office Action for EP Application No. 15706005.4 dated Sep. 21, 2017 (5 pages).
GE Healthcare, "Reliable Extraction of DNA from Whatman FTA Cards," 2010, https://www.gelifesciences.com/gehcls_images/GELS/RelatedContent/Files/1392818611307/litdoc28982222_20161015135424.pdf.
Kong et al., "Development of Cellulose-DNA Immunoadsorbent," Artificial Organs, 2002, 26(2):200-208.
Vaughan et al., "Purification of Plasmid DNA Using Corning Glass Fiber Filter Plates," 2001, http://csmedia2.corning.com/LifeSciences/Media/pdf/ddg_filterplaes_alsp_an_017.pdf.
International Search Report and Written Opinion regarding International Application No. PCT/EP2015/053620, dated Mar. 27, 2015, 11 pages.
Search Report Regarding GB application No. 1403522.4, dated Nov. 21, 2014, 3 pages.
Chinese Office Action for CN Application No. 201580010716.2 dated Mar. 11, 2019 (15 pages with English translation).

* cited by examiner

*Primary Examiner* — David C Thomas
(74) *Attorney, Agent, or Firm* — Eversheds Sutherland (US) LLP (57) ABSTRACT

A fluidic device is disclosed for processing a biological sample in order to extract nucleic acids contained in said sample and for subsequently amplifying said extracted nucleic acids, said device including a processed sample storage archive area 10 comprising an absorbent solid substrate 14 treated with at least one nucleic acid stabilizing reagent or reagent mix, said substrate allowing the generally dry and stabilized storage of said extracted and/or amplified nucleic acids, for example for long term storage of biological samples recovered forensically.

17 Claims, 7 Drawing Sheets

PROCESSED BIOLOGICAL SAMPLE STORAGE

CROSS-REFERENCE TO RELATED APPLICATIONS

This application is a filing under 35 U.S.C. 371 of international application number PCT/EP2015/053620, filed Feb. 20, 2015, which claims priority to GB application number 1403522.4, filed Feb. 28, 2014, the entire disclosures of each of which are hereby incorporated by reference.

FIELD OF THE INVENTION

The present invention relates to the storage of a sample processed within a fluidic device or the like.

BACKGROUND OF THE INVENTION

WO2010091414 describes a microfluidic device which can biochemically amplify DNA from a biological sample by polymerase chain reaction (PCR) and store, in liquid form, a portion of the sample that is not used in the PCR, in what is called a 'sample archive'. In that document it is proposed to seal the archive with paraffin wax for storage.

The present inventor has recognised that the storage arrangement described in WO2010091414 has drawbacks, particularly, in terms of sample stability, and the likely need for low temperatures during extended storage, and the use of liquid seals which can leak. The present inventor has also realised that there is a need to provide more a robust storage device, which allows storage of a processed biological sample at room temperature for many years if necessary, but which is low cost and very reliable. Such an improved storage device would, for example, be ideal for storing processed samples collected forensically from a crime scene.

SUMMARY

According to a first aspect, the present invention provides a fluidic device for processing a biological sample in order to extract nucleic acids contained in said sample and for subsequently amplifying said extracted nucleic acids, said device including a processed sample storage archive area comprising an absorbent solid substrate treated with at least one nucleic acid stabilising reagent or reagent mix, said substrate allowing the generally dry and stabilised storage of said extracted and/or amplified nucleic acids.

Herein, a processed biological sample is one which has been subjected to some chemical or biochemical process, for example, where a sample is initially a raw crime scene sample, then processing will include initial purification and/or elution of a that sample. Processing will also include subsequent steps such as PCR steps. So the scope of this invention includes storage of nucleic acids exacted from biological samples for example via purification and/or elution processing steps but which have not yet undergone a PCR, as well as those nucleic acids which have been exacted and amplified, for example via a PCR.

Herein, amplification of nucleic acids is not restricted to a PCR. Other known methods for multiplying or otherwise copying nucleic acids taken from biological samples are within the scope of this invention.

According to a second aspect, the invention further provides a processed biological sample storage archive for generally dry storage of a nucleic acids extracted from a processed biological sample, the archive comprising a generally dry absorbent solid substrate treated with at least one nucleic acid stabilising reagent or reagent mix, said substrate allowing the generally dry and stabilised storage of said extracted and/or amplified nucleic acids, said archive being adapted for removable mounted to the fluidic device according to the first aspect.

According to a third aspect, the invention provides a method of operating a biological sample processing fluidic device, in order to store a portion of the processed sample, the method comprising the following steps, in any suitable order: i) receiving a biological sample at a receiving chamber; ii) initially processing said sample, for example by purification and elution of nucleic acids in the sample; iii) directing a portion of said initially processed sample to a sample storage archive for generally dry storage of nucleic acids extracted from a biological sample, the archive comprising a generally dry absorbent solid substrate treated with at least one nucleic acid stabilising reagent or reagent mix; iv) optionally removing said storage archive and optionally removing the substrate from the remainder of the archive.

The invention is further characterised by the claims.

BRIEF DESCRIPTION OF THE DRAWINGS

The invention can be put into effect in numerous ways, illustrative embodiments of which are described below with reference to the drawings, wherein.

DETAILED DESCRIPTION OF THE INVENTION

Figure 1:
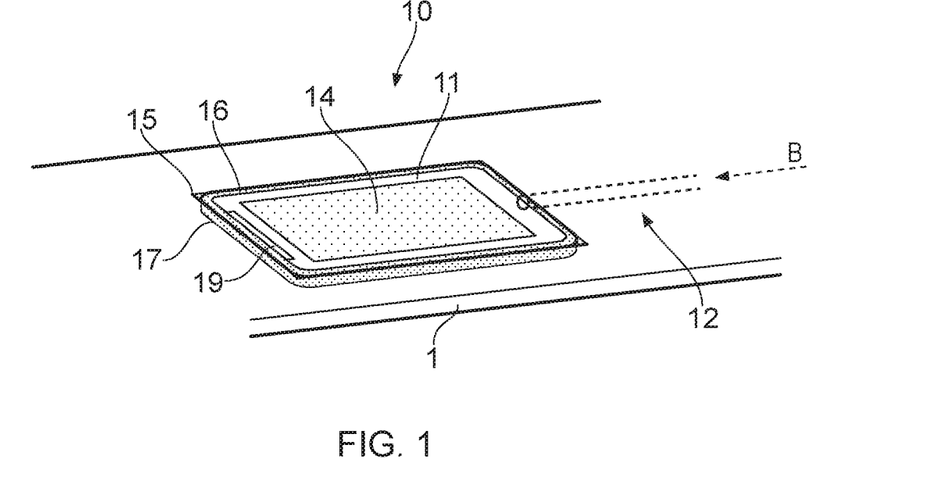
FIG. 1 shows a sample archive according to the invention, mounted to a fluidic device.

Referring to FIG. 1, a fluidic device 1, for example principally as disclosed in WO2010091414 includes a removable plastics sample archive chamber 10 housed on the device 1. The device 1 is shown transparently for clearer visibility of the archive 10, although in practice it is likely not to be so.

The archive chamber 10 sits inside the fluidic device 1, in this case a DNA analysis chipset. Typically, extraction and purification involve the use of silica, with a chaotrope and organic solvent to elute the nucleic acids. Following sample extraction/purification of nucleic acids, a predetermined amount of that processed sample is delivered to an amplification chamber for a PCR, to amplifying any extracted nucleic acids. The process involves an enzymatic reaction using oligonucleotide sequences and subsequent electrophoresis. The remaining portion of the sample is delivered to the archive chamber 10 along a fluid path 12 in the direction of arrow B, where it is absorbed onto a solid fibrous storage medium 14, in this case a treated cellulose paper-like matrix, for example as sold by Whatman Inc. under the trade name FTA®, housed releasably within the archive chamber 12. The archive chamber is formed from a plastics frame 11, which supports a flexible elastomeric seal 16 mounted to the periphery of the frame 11. The seal 16 removably holds the archive 10 in place on the device and includes upper and lower lips 15/17 which provide a fluid-tight vacuum seal between the archive 10 and the device 1.

Figure 2:
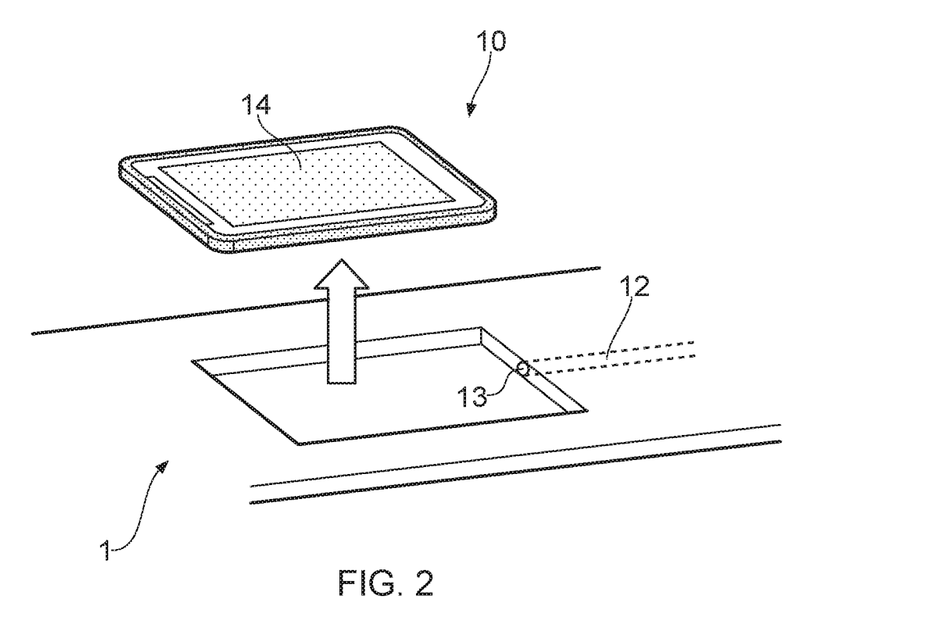
FIG. 2 shows another view of the sample archive shown in FIG. 1.

Referring additionally to FIG. 2, once the processing on the chipset is complete the archive chamber can be removed from the device 1. In order to remove the archive 10 from the device 1 an implement can be inserted into a recess 19 in order to lever it out. The relatively small archive chamber 10 is easier to store and handle than the entire chipset which can then be disposed of. If required, the processed sample now stored on the substrate 14 can be removed from the archive chamber 10 and used in downstream processing using standard analysis techniques or it can be stored for future use, possibly many years later. The sample archive allows for generally dry storage and retrieval of a purified DNA sample extracted from a sample being processed on the device.

In FIG. 2, an opening 13 of the fluid path 12 is visible which opens into the archive between the upper and lower lips and delivers the processed sample to the archive.

Figure 3:
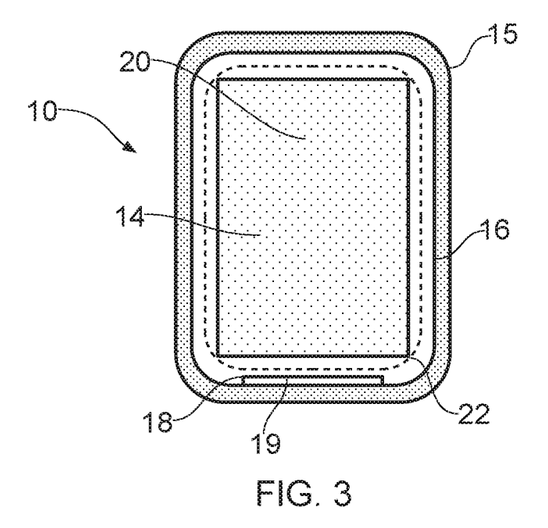
FIGS. 3 and 4 show top and bottom views respectively of the sample archive removed from the fluidic.

Referring to FIG. 3 the upper face of the now-removed archive 10 in shown. The archive 10 includes a transparent cover member 20 sealed to the frame 11 by a tamper-evident adhesive bond 22 around its periphery shown as a dotted line, so that it is evident that the cover member has, or has not been removed from the remaining archive. The adhesive bond 22 extends over the seal 16 also, so that it is possible to see whether or not the archive 10 has been removed from the device 1.

Figure 4:
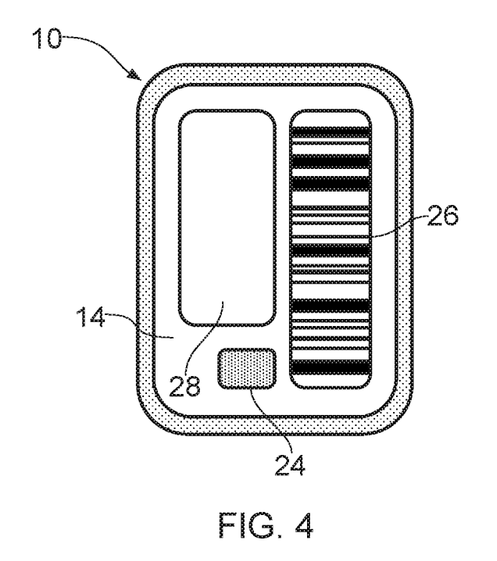

Referring to FIG. 4, the lower surface of the archive is shown. The archive includes an integrated RFID tag 24 that matches the identification of the microfluidic chipset 1, for sample tracking purposes. The archive chamber 10 also includes a barcode 26 for the same purposes. Also included is an area 28 for labelling with a sticky label, marker pen or other indicia.

Figure 5A:
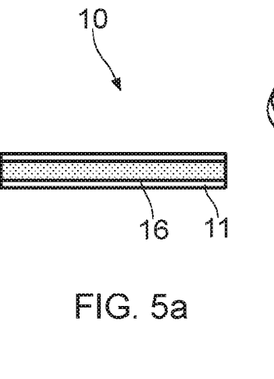
FIGS. 5a, b and c show side views of the sample archive.
Figure 5B:
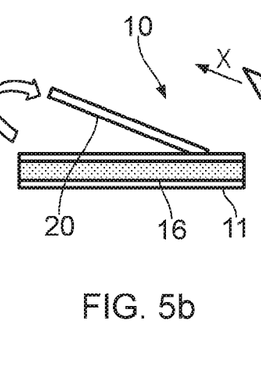
Figure 5C:
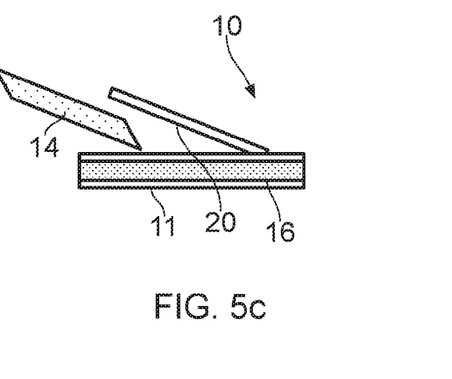

Referring to FIG. 5a, a side view of the archive 10 is shown schematically. In FIG. 5b, the cover member 20 is shown partially removed, and in FIG. 5c, the substrate 14 is shown removed in the direction of arrow X, from the remainder of the archive 10.

FIGS. 6 to 13 illustrate a method of processing a sample for use with the archive described above.

Figure 6:
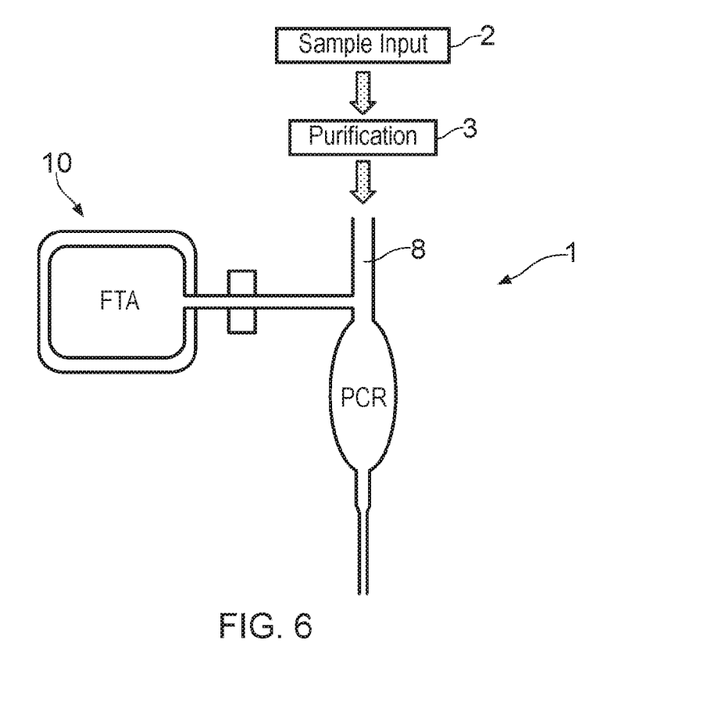
FIGS. 6 to 13 illustrate the method of use of the sample archive shown in the previous figures.

FIG. 6: according to the method, a DNA sample, for example from a buccal swab or a blood sample, is deposited into a receiving chamber 2 of a fluidic device 1, in this case a microfluidic processing chipset, for processing. The sample is purified at a downstream location 3, in this case by binding the DNA to a membrane, and carrying out multiple washing steps. The purified DNA is eluted from the membrane into a channel 8.

Figure 7:
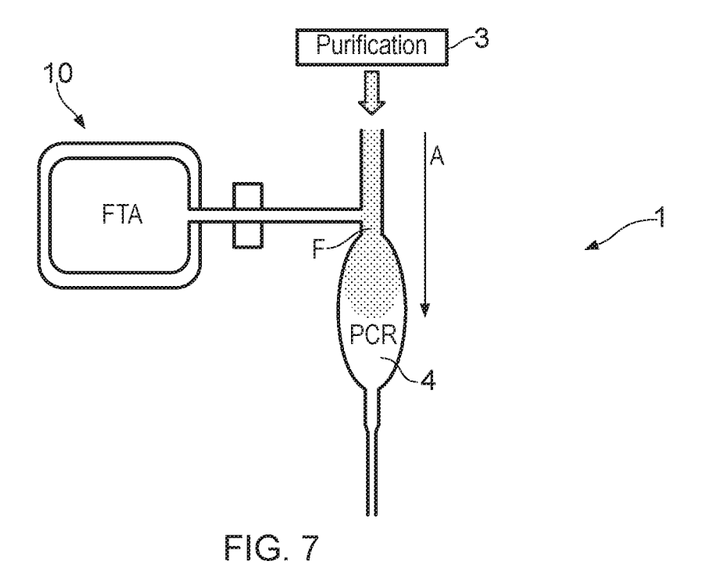

FIG. 7: The processed sample in the form of eluted fluid F flows through the channel 8 in the direction of arrow A and then into a PCR chamber 4.

Figure 8:
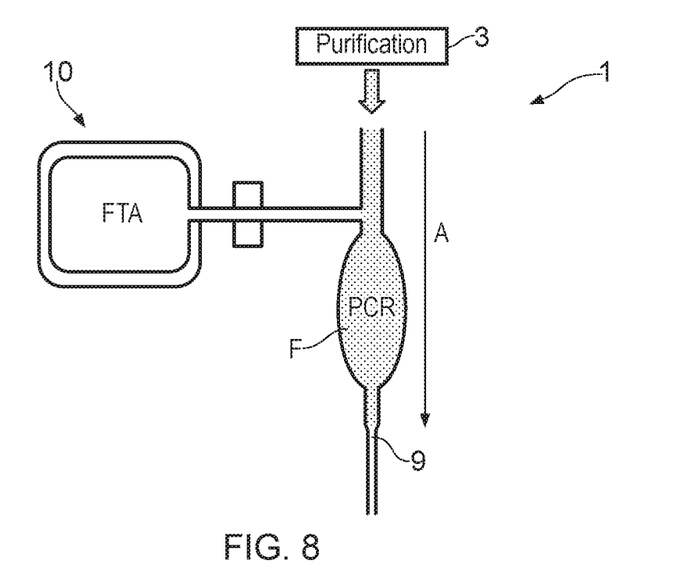

FIG. 8: The PCR chamber 4 fills and becomes choked at its narrow exit 9.

Figure 9:
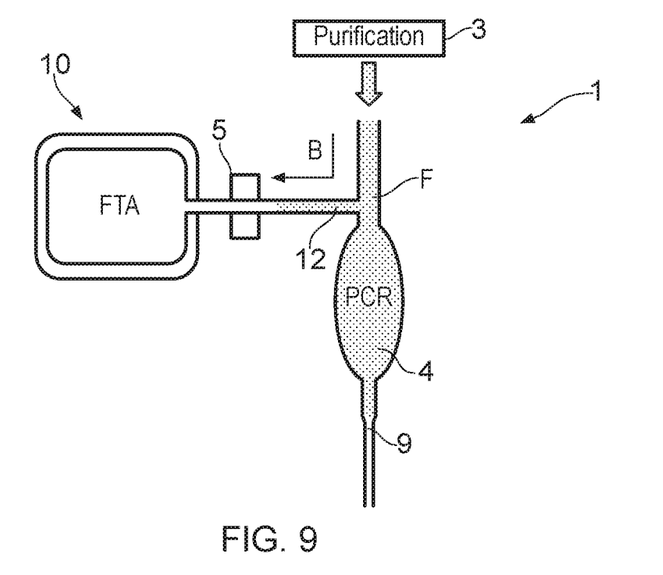

FIG. 9: The choking of the PCR chamber 4 prompts the flow of further processed sample fluid F to divert into the channel 12 in the direction of arrow B toward an open valve 5.

Figure 10:
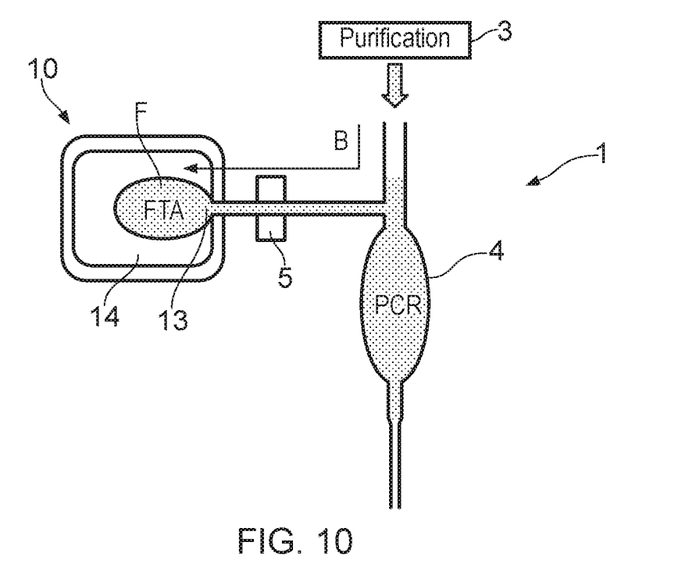

FIG. 10: The fluid F flows past the open valve 5 and into the archive chamber 10 at the opening 13 where it is absorbed on the substrate 14, in this case FTA paper as described above.

Figure 11:
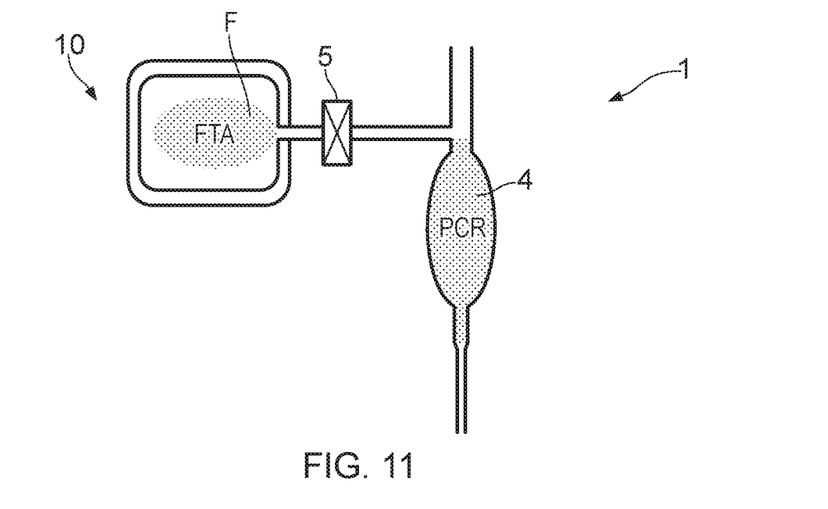

FIG. 11: The valve 5 is closed, to seal the archive 10.

Figure 12:
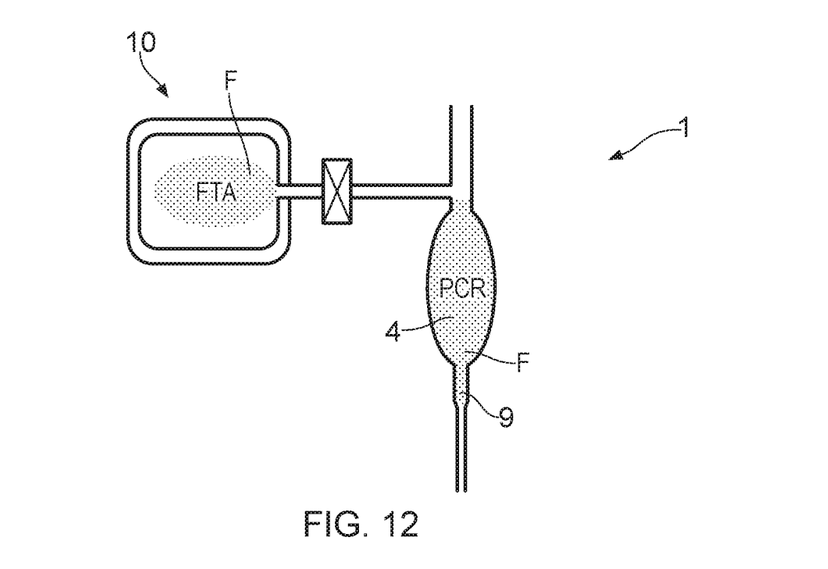

FIG. 12: The processed sample F is further processed by a PCR to amplify any nucleic acids in the sample fluid, for example according to known thermo-cycling and enzymatic techniques.

Figure 13:
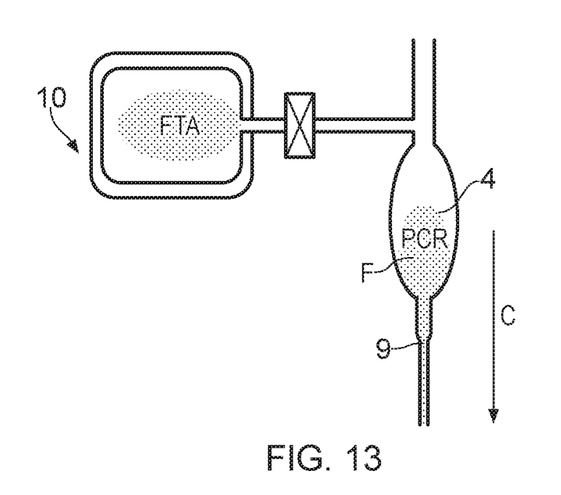

FIG. 13 The further processed sample fluid F exits the PCR chamber 4 at exit 9, for yet further processing, for example electrophoretic separation. The sample archive 10 can remain in the microfluidic device, or it can be removed as described above.

Although embodiments have been described and illustrated above, it will be apparent to the skilled addressee that additions, omissions and modifications are possible to those embodiments without departing from the scope of the invention claimed. For example, although this invention can be implemented onto a microfluidic device which employs just a few milliliters of fluid, to allow recovery of a processed sample rather than sending the excess processed sample to waste, any fluidic device can utilise this invention. If used in a microfluidic device, this invention will be useful in forensics, in particular for crime scene samples, where the sampling opportunities may be limited, thereby preserving the sample. It will allow the same sample to be reinvestigated if a sample were to fail the initial analysis, but it would also give the option to perform other forensic analysis tests on the same sample such as mitochondrial DNA, YSTR, SNP analysis. The fact that the sample is initially processed, for example purified, will save time and cost of performing these extra tests.

One specific example of the substrate 14 has been given as FTA®, which has been chosen because its treatment inhibits the degradation of DNA. In one embodiment, the substrate treatment is wet-applied stabilising reagents in the form of combination of a weak base, and a chelating agent, optionally, uric acid or a urate salt, and optionally an anionic surfactant.

It is preferred that the weak base is a Lewis base which has a pH of about 6 to 10, preferably about pH 8 to 9.5.

Alternatively, the weak base is an organic and inorganic base, and if inorganic then optionally includes an alkali metal carbonate, bicarbonate, phosphate or borate (e.g. sodium, lithium, or potassium carbonate), and if organic then optionally includes, tris-hydroxymethyl amino methane (Tris), ethanolamine, tri-ethanolamine and glycine and alkaline salts of organic acids (e.g. trisodium citrate).

Alternatively, the weak base is Tris present either as a free base or as a salt, for example, a carbonate salt.

Preferably, the chelating agent binds multivalent metal ions with a comparable or better affinity than ethylene diamine tetraacetic acid (EDTA), and is preferably EDTA.

Preferably, the anionic surfactant includes a hydrocarbon moiety, aliphatic or aromatic, containing one or more anionic groups.

Preferably, the anionic surfactant is a detergent, for example sodium dodecyl sulphate (SDS) and/or sodium lauryl sarcosinate (SLS).

Other stabilising reagents could be employed, for example a chaotropic substance such as a chaotropic salt, for example guanidinium thiocyanate.

The substrate 14 is treated with the stabilising reagents mentioned above so as to be capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any downstream processing. It will be apparent to the skilled addressee that other reagent mixes could perform one or more of the functions mentioned above.

It is possible that the processed sample could be stored in the archive after PCR amplification, where an amplified or otherwise copied DNA sequence is required.

The invention claimed is:

1. A fluidic device for processing a biological sample in order to extract and process nucleic acids contained in said sample and for subsequently amplifying said extracted and processed nucleic acids, said device including a processed sample storage archive area comprising an absorbent solid substrate treated with at least one nucleic acid stabilizing reagent or reagent mix, said substrate allowing the generally dry and stabilized storage of said processed extracted and/or amplified nucleic acids.

2. A processed biological sample storage archive for generally dry storage of a nucleic acids extracted from a processed biological sample, the archive comprising a generally dry absorbent solid substrate treated with at least one nucleic acid stabilizing reagent or reagent mix, said substrate allowing the generally dry and stabilized storage of said processed extracted and/or amplified nucleic acids, said archive being adapted for removable mounting to the fluidic device of claim 1.

3. The fluidic device as claimed in claim 1, wherein said stabilizing reagent or reagent mix comprises: a weak base, and a chelating agent, optionally, uric acid or a urate salt, and optionally an anionic surfactant.

4. The fluidic device as claimed in claim 1, wherein said stabilizing reagent or reagent mix comprises a chaotropic substance.

5. The sample storage archive as claimed in claim 2 further comprising a plastic frame and an elastomeric seal mounted generally peripherally on the frame for sealing the frame to the device and for providing said removable mounting.

6. The sample storage archive as claimed in claim 5, wherein said substrate is located within the plastic frame and the sample archive further includes a removable cover.

7. The sample storage archive as claimed in claim 6, further comprising identification means, including one or more of: an RFID (radio-frequency identification) tag; a barcode; and an area for accepting indicia.

8. A method of operating a biological sample processing fluidic device, in order to store a portion of a sample processed by said device, the method comprising the steps, in any suitable order, of:
   i) receiving a biological sample at a receiving chamber;
   ii) initially processing said sample, at least by one of purification and elution of nucleic acids in the sample;
   iii) directing a portion of said initially processed sample to a sample storage archive for generally dry storage of nucleic acids extracted from a biological sample, the archive comprising a generally dry absorbent solid substrate treated with at least one nucleic acid stabilizing reagent or reagent mix;
   iv) optionally removing said storage archive and optionally removing the substrate from the remainder of the archive.

9. A processed biological sample storage archive for generally dry storage of a nucleic acids extracted from a processed biological sample, the archive comprising a generally dry absorbent solid substrate treated with at least one nucleic acid stabilizing reagent or reagent mix, said substrate allowing the generally dry and stabilized storage of processed extracted and/or amplified nucleic acids,
   wherein the sample storage archive further comprises a plastic frame and an elastomeric seal mounted generally peripherally on the frame for sealing the frame to the device and for providing removable mounting to a fluidic device, and
   wherein said substrate is located within the plastic frame and the sample archive further includes a removable cover.

10. The processed biological sample storage archive as claimed in claim 9, wherein the generally dry absorbent solid substrate further comprises the processed extracted and/or amplified nucleic acids.

11. The processed biological sample storage archive as claimed in claim 9, wherein the processed extracted and/or amplified nucleic acids comprise purified extracted and/or amplified nucleic acids.

12. The processed biological sample storage archive as claimed in claim 9, wherein said substrate is configured to allow the generally dry and stabilized storage of said processed extracted and/or amplified nucleic acids at room temperature.

13. The fluidic device as claimed in claim 1, wherein the generally dry absorbent solid substrate further comprises the processed extracted and/or amplified nucleic acids.

14. The fluidic device as claimed in claim 1, wherein the process comprises purification, and processed extracted and/or amplified nucleic acids comprise purified extracted and/or amplified nucleic acids.

15. The fluidic device as claimed in claim 1, wherein said substrate is configured to allow the generally dry and stabilized storage of said processed extracted and/or amplified nucleic acids at room temperature.

16. The fluidic device as claimed in claim 4, wherein the chaotropic substance comprises guanidinium thiocyanate.

17. The fluidic device as claimed in claim 16, wherein the at least one chaotropic salt comprises at least one chaotropic salt.

* * * * *